United States Patent [19]

Dilly et al.

[11] Patent Number: 5,667,994

[45] Date of Patent: Sep. 16, 1997

[54] **AMPLIFICATION AND DETECTION OF *MYCOBACTERIUM AVIUM* COMPLEX SPECIES**

[75] Inventors: Karen Ann Dilly, Sparks; Silvia A. Bustos, Catonsville; Christine Ann Rostkowski; Dolores M. Berger, both of Baltimore, all of Md.

[73] Assignee: Becton, Dickinson and Company, Franklin Lakes, N.J.

[21] Appl. No.: 608,584

[22] Filed: Feb. 28, 1996

[51] Int. Cl.$^6$ ................................................ C12P 19/34
[52] U.S. Cl. ............... 435/91.2; 435/91.1; 435/6; 536/24.3
[58] Field of Search .............. 536/24.3; 435/91.2, 435/6, 91.1

[56] References Cited

U.S. PATENT DOCUMENTS

| | | | |
|---|---|---|---|
| 5,314,801 | 5/1994 | Nycz et al. | 435/6 |
| 5,500,341 | 3/1996 | Spears | 435/6 |
| 5,523,204 | 6/1996 | Singer et al. | 435/5 |
| 5,550,025 | 8/1996 | Walker | 435/6 |

OTHER PUBLICATIONS

S. Takewaki, et al. "Nucleotide Sequence Comparison of the Mycobacterial dnaJ Gene and PCR–Restriction Fragment Length Polymorphism Analysis for Identification of Mycobacterial Species" *Int. J. Sys. Bact.* 44:159–166 (1994).

M. Yang, et al. "Isolation of a DNA Probe for identification of Mycobacterium kansasii, including the Genetic Subgroup" *J. Clin. Microbiol.* 31:2769–2772 (1993).

R. Lathigra, et al. "A gene from Mycobacterium tuberculosis which is homologous to the Dna J heat shock protein of E. coli" *Nucl. Acids Res.* 16:1636 (1988).

S. Takewaki, et al. "Genus–Specific Polymerase Chain Reaction for the Mycobacterial dnaJ Gene and Species–Specific Oligonucleotide Probles" *J. Clin. Microbiol.* 31:446–450 (1993).

*Primary Examiner*—Kenneth R. Horlick
*Assistant Examiner*—Joyce Tung
*Attorney, Agent, or Firm*—Donna R. Fugit

[57] ABSTRACT

Amplification primers and methods for complex-specific amplification of target sequences in the dnaJ genes of the *Mycobacterium avium* Complex (MAC) species are disclosed. The primer target binding sequences are useful for amplification of the dnaJ target in a variety of amplification reactions, with detection of the complex-specific target and, optionally, identification of the MAC species from which the target is derived. Primers and methods for multiplex amplification of dnaJ and a second target are also described.

26 Claims, No Drawings

AMPLIFICATION AND DETECTION OF *MYCOBACTERIUM AVIUM* COMPLEX SPECIES

FIELD OF THE INVENTION

The present invention relates to amplification and detection of target nucleic acid sequences. In particular, the invention relates to amplification and detection of target nucleic acid sequences in Mycobacteria.

BACKGROUND OF THE INVENTION

The Mycobacteria are a genus of bacteria which are acid-fast, non-motile, gram-positive rods. The genus comprises several species which include, but are not limited to, *Mycobacterium africanum, M. avium, M. bovis, M. bovis-BCG, M. chelonae, M. fortuitum, M. gordonae, M. intracellulare, M. kansasii, M. microti, M. scrofulaceum, M. paratuberculosis* and *M. tuberculosis*. Certain of these organisms are the causative agents of disease. For the first time since 1953, cases of mycobacterial infections are increasing in the United States. Although tuberculosis is of particular concern, other mycobacterial infections are also increasing as a result of an increase in the number of immune compromised patients. Many of these new cases are related to the AIDS epidemic, which provides an immune compromised population which is particularly susceptible to infection by Mycobacteria. *Mycobacterium avium, Mycobacterium kansasii* and other non-tuberculosis mycobacteria are found as opportunistic pathogens in HIV infected and other immune compromised patients.

*M. avium* and *M. intracellulare* are members of the *Mycobacterium avium* complex (MAC). *M. paratuberculosis* is a subspecies of *M. avium* and is also generally included in the MAC. These species have become important in recent years because of the high prevalence of disseminated MAC infection in AIDS patients. The *Mycobacterium avium* complex is comprised of 28 serovars which are distinguishable on the basis of their biochemical and seroagglutination characteristics (see review by Inderlied, et al. 1993. *Clin. Microbial. Rev.* 6, 266–310). Depending on the method of classification, 10–12 of the 28 serovars are classified as belonging to the species *Mycobacterium avium*, and 10–12 belong to the species *Mycobacterium intracellulare*. Six of the MAC serovars have not yet been definitively classified. MAC infections currently account for approximately 50% of the pathogenic isolates identified by mycobacteriology labs and are most common among AIDS and other immunocompromised patients. Early diagnosis and treatment of MAC infections can improve and prolong the lives of infected individuals.

The diagnosis of mycobacterial infections has traditionally been dependent on acid-fast staining and cultivation of the organism, followed by biochemical assays. These procedures are time-consuming, and a typical diagnosis using conventional culture methods can take as long as six weeks. Automated culturing systems such as the BACTEC™ system (Becton Dickinson Microbiology Systems, Sparks, Md.) can decrease the time for diagnosis to one to two weeks. However, there is still a need to reduce the time required for diagnosing Mycobacterial infections to less than a week, preferably to one day or less. Nucleic acid amplification is a powerful technology which allows rapid detection of specific target sequences. It is therefore a promising technology for rapid detection and identification of Mycobacteria. Examples of nucleic acid amplification technologies known in the art are Polymerase Chain Reaction (PCR: U.S. Pat. Nos. 4,683,195; 4,683,202; 4,800,159; 4,965,188), Strand Displacement Amplification (SDA—G. Walker, et al. 1992. *Proc. Nat. Acad. Sci. U.S.A.* 89, 392–396; G. Walker, et al. 1992. *Nucl. Acids Res.* 20, 1691–1696; U.S. Pat. No. 5,270,184; U.S. Pat. No. 5,455,166; published European Patent Application No. 0 684 315), nucleic acid sequence based amplification (NASBA: U.S. Pat. No. 5,130,238 to Cangene), transcription based amplification (TAS—D. Kwoh, et al. 1989. *Proc. Nat. Acad Sci. U.S.A.* 86, 1173–1177), self-sustained sequence replication (3SR: J. Guatelli, et al. 1990. *Proc. Nat. Acad Sci. U.S.A.* 87, 1874–1878) and the Qβ replicase system (P. Lizardi, et al. 1988. *BioTechnology* 6, 1197–1202).

Isothermal amplification methods such as SDA and 3 SR have particular advantages in diagnostics, as they do not require the high/low temperature cycling characteristic of methods such as the PCR. They are therefore simpler protocols and require less specialized equipment to perform. However, isothermal amplification methods such as SDA generally are not capable of amplifying targets as large as those amplifiable by PCR. Small target sequences severely restrict the ability to design primers and probes with the desired specificity for detection of a given target because the proximity of appropriate amplification primer binding sites becomes a factor and there is less sequence available in the amplification product for assay probe design.

Initially, SDA was developed for use at temperatures between about 35° C. and 45° C. ("conventional SDA"). Recently, it has been adapted to higher temperatures using thermophilic polymerases and restriction endonucleases ("thermophilic SDA" or "tSDA") as described in published European Patent Application No. 0 684 315. The tSDA system provides the advantages of increased speed and specificity as compared to conventional SDA. While the target binding sequences of amplification primers designed for use in conventional SDA generally will function in tSDA, they are usually shorter and amplification efficiency may therefore be reduced at the higher temperatures of tSDA. Also, as is the case for primer design in conventional SDA, apparently minor modifications in the target binding sequence of primers for tSDA (such as lengthening it) often have unpredictable effects on amplification efficiency. In contrast, primers comprising the target binding sequences of primers designed for tSDA usually function efficiently when adapted to amplification primers for conventional SDA or other amplification reactions.

The heat shock proteins are a family of proteins which are expressed in elevated amounts when an organism is challenged by an increase in temperature. The heat shock proteins are highly conserved (R. J. Garcia, et al. 1989. *Infection and Immunity* 57, 204–212; R. S. Gupta, et al. 1992. *J. Bacteriology* 174, 4594–4605). The dnaJ gene codes for a 42 kd heat-shock protein believed to be involved in the cellular stress response. *M. tuberculosis* was the first of the mycobacteria for which the nucleotide sequence of the dnaJ gene was determined (R. B. Lathigra, et al. 1988. *Nucl. Acids Res.* 16, 1636). The nucleotide sequence of a segment of the dnaJ gene of *M. leprae* was subsequently determined (S. S. Harvey, et al. 1993. *J. Gen. Microbial.* 139, 2003–2008). Later, using the *M. tuberculosis* sequence published by R. B. Lathigra et al., supra, S. I. Takewaki, et al. (1993. *J. Clin. Microbiol.* 31, 446–450) developed a set of genus-specific PCR primers which amplify a 236-bp fragment of the dnaJ gene (bp 1394–1629) from a broad range of mycobacterial species, including *M. avium* and *M. intracellulare*. Species-specific oligonucleotide probes which allowed identification of *M. tuberculosis, M. avium, M.* intracellulare, and *M. kansasii* following genus-specific amplification by PCR were also reported. The dnaJ gene of nineteen species of mycobacteria was then sequenced and used to determine phylogenetic relationships and to differentiate species on the basis of species-specific restriction sites in the gene (S. I. Takewaki, et al. 1994. *Int. J. Syst. Bacteriol.* 44, 159–166). Japanese Kokai Patent No. 6-133775 (Takewaki, et al., published May 17, 1994) discloses a genus-specific amplification primer pair for PCR and several species-specific probes derived from the dnaJ gene of mycobacteria.

Certain terms used herein are defined as follows:

An amplification primer is a primer for amplification of a target sequence by extension of the primer after hybridization to the target sequence. The 3' end of an SDA amplification primer (the target binding sequence) hybridizes at the 3' end of the target sequence. The target binding sequence confers target specificity on the amplification primer. The SDA amplification primer further comprises a recognition site for a restriction endonuclease near its 5' end. The recognition site is for a restriction endonuclease which will nick one strand of a DNA duplex when the recognition site is hemimodified, as described by G. Walker, et al. (1992. *PNAS*, supra). The SDA amplification primer may also be referred to as the "S" primer (e.g., $S_1$ and $S_2$ when a pair of amplification primers is used for amplification of a double stranded sequence). For amplification methods which do not require specialized sequences at the ends of the target, the amplification primer generally consists essentially of only the target binding sequence. For example, amplification of a target sequence according to the invention using the PCR will employ amplification primers consisting of the target binding sequences of the amplification primers in Table 1. For amplification methods which require specialized sequences other than a restriction endonuclease recognition site appended to the target (e.g., an RNA polymerase promoter for 3SR, NASBA or transcription based amplification), the required specialized sequence may be linked to the target binding sequence shown in Table 1 using routine methods such as chemical synthesis for preparation of the oligonucleotides.

A bumper primer or external primer is a primer used to generate targets which can be amplified by SDA. The bumper primer anneals to a target sequence upstream of the amplification primer such that extension of the bumper primer displaces the downstream amplification primer and its extension product. Bumper primers may also be referred to as "B" primers (e.g., $B_1$ and $B_2$ when a pair of bumper primers is used to displace the extension products of a pair of amplification primers). Extension of bumper primers is one method for displacing the extension products of amplification primers, but heating is also suitable in certain amplification reactions.

The terms target or target sequence refer to nucleic acid sequences to be amplified. These include the original nucleic acid sequence to be amplified, the complementary second strand of the original nucleic acid sequence to be amplified, and either strand of a copy of the original sequence which is produced by the amplification reaction. These copies also serve as amplifiable target sequences by virtue of the fact that they comprise copies of the original target sequences to which the amplification primers hybridize.

Copies of the target sequence which are generated during the amplification reaction are referred to as amplification products, amplimers or amplicons.

The term extension product refers to the single-stranded copy of a target sequence produced by hybridization of an amplification primer and extension of the amplification primer by polymerase using the target sequence as a template.

The term assay probe refers to any of the oligonucleotides used in the detection or identification portion of an assay. In the present invention, the assay probes are probes used for complex-, group- or species-specific detection or identification of Mycobacteria. Detector probes and capture probes are examples of assay probes.

The assay region or assay region sequence is the portion of a target sequence, or other nucleic acid, to which an assay probe hybridizes.

The term species-specific refers to detection or amplification in a species of organism without substantial detection or amplification in other species of the same genus or species of a different genus. Genus-specific refers to detection or amplification in the majority of the species of a genus, without substantial detection or amplification in the species of a different genus. Group- or complex-specific refers to detection or amplification in a majority of related species in a selected group (e.g., MAC) without substantial detection or amplification in other species of the same genus or species of a different genus.

SUMMARY OF THE INVENTION

The present invention provides oligonucleotide primers which may be used for complex-specific amplification of a target sequence found in all 28 serovars comprising the MAC. The target sequence is a segment of the dnaJ gene. Thus, a single pair of amplification piers enables amplification of a target sequence from the dnaJ gene of both *M. avium* and *M. intracellulare*. These amplification primers have been designed for high-efficiency, high-specificity amplification at increased temperatures, such as in tSDA and the PCR, however, they are also useful in lower-temperature amplification reactions such as conventional SDA, 3SR or NASBA. Oligonucleotide assay probes which hybridize to the assay region of the amplified target are used to detect the amplification products, optionally distinguishing between the MAC species. The inventive methods also allow detection of the dnaJ target sequence in *Mycobacterium paratuberculosis*, the subspecies of *M. avium* associated with Crohn's disease in humans and Johne's disease in livestock.

DETAILED DESCRIPTION OF THE INVENTION

Amplification primers which allow complex-specific amplification of a target fragment of the dnaJ gene of MAC species are provided. The efficient amplification of targets in both *M. avium* and *M. intracellulare* was not predicted based on the sequence data of S. I. Takewaki, et al. (1994, supra), as the sequences of *M. avium* and *M. intracellulare* differ by one to two nucleotides in the region where the amplification primers hybridize. Mismatches between the target binding sequences of primers and the sequences to which they hybridize in the target generally inhibit or otherwise interfere with target amplification. The present invention also provides oligonucleotide probes and primers which are particularly useful for amplification of MAC-specific targets in the dnaJ gene by thermophilic Strand Displacement Amplification (tSDA). The amplified target may be detected as an indication of the presence of a MAC species or to identify the particular MAC species which is present. It has been discovered that the primers of the invention efficiently amplify both *M. avium* and *M. intracellulare* targets in spite of nucleotide sequence differences between these species at the site of amplification primer hybridization in the targets. The target in *M. avium* is amplified at least about $10^6$-fold using the primers of the invention. In addition, following amplification, the amplified *M. avium* and *M. intracellulare* target sequences may be distinguished from each other by hybridization to the assay probes of the invention.

Initially, the dnaJ genes of *M. avium* and *M. intracellulare* were amplified by PCR using Primer #3 of Takewaki, et al., 1993, supra, and a second primer based on nucleotides 1730–1751 of the *M. tuberculosis* dnaJ sequence described by Lathigra, et al., supra. The amplification products were then sequenced to include a region beyond the sequences published by Takewaki, et al., 1994, supra, and the sequences thus obtained were aligned for primer design. Primers developed for use with tSDA are shown in Table 1. Also shown are probes for detection of the MAC targets. The exemplary restriction endonuclease recognition sites in the amplification primers (BsoBI) are bolded and the target binding sequences are italicized. The target binding sequence of an amplification primer determines its target specificity. The dnaJ sequences to which the amplification primers hybridize in *M. avium* and *M. intracellulare* differ by one to two nucleotides at each end of the target. All but one of the amplification primers (SEQ ID NO:7) was designed such that the target binding sequence hybridizes to one of the two targets (either *M. avium* or *M. intracellulare*) with perfect Watson-Crick complementary, but exhibits a 1–2 nucleotide mismatch when hybridized to the target in the other species. For example, the target binding sequence of SEQ ID NO:1 hybridizes to the *M. intracellulare* target with perfect complementarity but hybridizes to the *M. avium* target with a single nucleotide mismatch. The target binding sequences of SEQ ID NOs:2–4 have a two nucleotide mismatch with *M. avium*. Similarly, the target binding sequence of SEQ ID NOs:5–6 hybridize to the *M. intracellulare* target with perfect complementarity but hybridize to the *M. avium* target with a single nucleotide mismatch. SEQ ID NO:7 has a single nucleotide mismatch with the target of each species.

The presence of nucleotide mismatches would be expected to destabilize the primer-target complex as compared to a perfectly complementary complex, but, unexpectedly, did not appear to significantly reduce amplification efficiency. Initial hybridization of amplification primers to a target sequence in an amplification reaction and extension of the amplification primers produces copies of the desired target sequence flanked by perfectly complementary sequences contributed by the amplification primers. Mismatches are therefore corrected and these terminally-modified targets are amplified. Thus, the terminal sequences of the modified targets in both *M. avium* and *M. intracellulare* will become identical, but the assay regions between the sequences which bind the amplification primers will remain unchanged, allowing the amplification products of *M. avium* and *M. intracellulare* to be distinguished. Applicants hypothesize that this unique feature of nucleic acid amplification allows the amplification reaction to overcome the detrimental effects of primer/target mismatches as long as there is sufficient hybridization of the mismatched primer to the target to generate a modified target suitable for amplification. This may account for the high efficiency of amplification observed in this system in spite of the mismatch. Using the amplification primers and bumper primers listed in Table I, the dnaJ targets of *M. avium* and *M. intracellulare* can be amplified at least about $10^6$-fold by tSDA, permitting detection of as few as 100 initial copies of the target in *M. avium* and 1000 initial copies of the target in *M. intracellulare*. The greater sensitivity for detection of *M. avium* was unexpected in view of the mismatches in the primers. Further routine optimization of the amplification and detection reaction conditions would be expected to even further increase assay sensitivity.

The amplification primers of the invention are also useful in other nucleic acid amplification protocols such as the PCR, conventional SDA (a reaction scheme which is essentially the same as that of tSDA but conducted at lower temperatures), 3SR, NASBA and TAS. Specifically, any amplification protocol which utilizes cyclic, specific hybridization of primers to the target sequence, extension of the

TABLE 1

| Amplification Primers | |
|---|---|
| Upstream Primers | |
| Prim1-1T | 5'CGATTCCGCTCCAGACTTCTCGGGG*CCGGTGAACGA*3' (SEQ ID NO:1) |
| Prim1-2T | 5'CGATTCCGCTCCAGACTTCTCGGGC*GCCGGTGAACGA*3' (SEQ ID NO:2) |
| Prim1-3T | 5'CGATTCCGCTCCAGACTTCTCGGGC*CGCCGGTGAACGA*3' (SEQ ID NO:3) |
| Prim1-4T | 5'CGATTCCGCTCCAGACTTCTCGGGG*CCGCCGGTGAACGA*3' (SEQ ID NO:4) |
| Downstream Primers | |
| IN2B-1T | 5'ACCGCATCGAATGCATGTCTCGGG*CGGACAACACGTTG*3' (SEQ ID NO:5) |
| IN2B-2T | 5'ACCGCATCGAATGCATGTCTCGGG*TCGGACAACACGTTG*3' (SEQ ID NO:6) |
| IN2B-3T | 5'ACCGCATCGAATGCATGTCTCGGGG*TCGGACAACACGTTG*3' (SEQ ID NO:7) |
| Bumper Primers | |
| BUMP2.1 | 5'TTCCTTGCGCTTGG3' (SEQ ID NO:8) |
| BUMP3.1 | 5'GCCAACCCGGACAA3' (SEQ ID NO:9) |
| Capture Probes | |
| MAI33 | 3Biotin-5'GTGCGCCTCCGAC3' (*M. intracellulare*) (SEQ ID NO:10) |
| MAI37 | 5'ACCGCCTTGAATC3'-3Biotin (*M. avium*) (SEQ ID NO:11) |
| Detector Probes | |
| MAI36 | 5'ACGGCTTTGAATC3'-AP (*M. intracellulare*) (SEQ ID NO:12) |
| MAI38 | AP-5'GTGCGCCTCGGAG3' (*M. avium*) (SEQ ID NO:13) |
| DAV | 5'TTCAAGGCGGTCTCC3 (SEQ ID NO:14) |
| DIN | 5'TTCAAAGCCGTGTCG3' (SEQ ID NO:15) | primers using the target sequence as a template and separation or displacement of the extension products from the target sequence may employ the amplification primers of the invention. For amplification methods which do not require specialized, non-target binding sequences (e.g., PCR), the amplification primers may consist only of the target binding sequences of the amplification primers listed in Table 1. The primer sequences illustrated in Table 1 comprise a specialized, non-target binding sequence (the restriction endonuclease recognition site) which is required for SDA and is appended to the target in the target generation reaction which precedes amplification by SDA. Amplification methods which require other specialized, non-target binding sequences linked to the target (e.g., the RNA polymerase promoter required by 3SR, NASBA and TAS) may employ amplification primers comprising the target binding sequences disclosed herein appended to the sequence required by the selected amplification method. Similarly, a restriction endonuclease recognition site appropriate for conventional SDA may be substituted for the exemplified BsoBI site as is known in the art, or a different restriction endonuclease recognition site appropriate for tSDA may be substituted when the target is amplified by thermophilic SDA. Adaptation of the target binding sequences of the invention to amplification methods other than SDA employs routine methods for preparation of amplification primers, such as chemical synthesis, and the well known structural requirements for the primers of the selected amplification reaction. The target binding sequences of the invention may therefore be readily adapted to MAC-specific target amplification and detection in a variety of amplification reactions using only routine methods for production, screening and optimization.

The primers of the invention are also useful in amplification reactions in which multiple, different targets are simultaneously amplified (multiplex amplification or multiplexing). For example, multiplex amplification using SDA is described in U.S. Pat. No. 5,470,723 and U.S. Pat. No. 5,422,252, the disclosures of which are hereby incorporated by reference. As disclosed therein, using adapter primers a terminal sequence of the dnaJ target may be appended to one end of a second target, and a terminal sequence of the second target may be appended to one end of the dnaJ target. For example, to produce an adapter primer the 5' end of the target binding sequence of a dnaJ amplification primer disclosed herein may be linked to an adapter sequence which is substantially identical to the target binding sequence of an amplification primer for the second target. For the second target, the adapter primer comprises a 3' target binding sequence which hybridizes to the second target and a 5' sequence which is substantially identical to the target binding sequence of an amplification primer for dnaJ. After appending a terminal segment of each target to one end of the other, they may both be amplified using a single pair of amplification primers comprised of the dnaJ amplification primer and the amplification primer for the second target. For example, the primers of the invention may be used with IS6110 amplification primers and appropriate adapter primers to simultaneously amplify M. tuberculosis-specific and MAC-specific targets with identification of the group or species in the detection portion of the assay. Alternatively, the primers of the invention may be used with 16S primers and appropriate adapter primers to simultaneously amplify Mycobacterium genus-specific and MAC-specific targets, with group-specific identification of MAC or genus-specific identification of Mycobacteria in the detection portion of the assay.

The structure and function of the primers used in adapter-mediated multiplexing are described in U.S. Pat. No. 5,470,723 and U.S. Pat. No. 5,422,252. Using these teachings, the target binding sequences of the dnaJ amplification primers of the invention may be appended to adapter sequences using routine methods for primer construction and used for multiplex amplification of the dnaJ target and any selected second target. For example, the primers of the invention and the primers of the above patents may be adapted for tSDA multiplex amplification of MAC-specific targets (dnaJ) and M. tuberculosis species-specific targets (IS6110) as shown in Table 2. Target binding sequences are italicized, restriction endonuclease recognition sites are bolded and adapter sequences are underlined:

TABLE 2

MULTIPLEX PRIMER SET 1 dnaJ Adapter Primer
AAGGCGTACTCGACCGCCGGTGAACGA (SEQ ID NO:16)
dnaJ Amplification Primer
CGATTCCGCTCCAGACTTCTCGGG*TCGGACAACACGTTG* (SEQ ID NO:17)
M. tb Adapter Primer
TCGGACAACACGTTG*GTACTGAGATCCCCT* (SEQ ID NO:18)
M. tb Amplification Primer
ACCGCATCGAATGCATGTCTCGGG*TAAGGCGTACTCGACC* (SEQ ID NO:19)

MULTIPLEX PRIMER SET 2 dnaJ Adapter Primer
AAGGCGTACTCGACC*TCGGACAACACGTTG* (SEQ ID NO:20)
dnaJ Amplification Primer
(SEQ ID NO:1)
M. tb Adapter Primer
GCCGGTGAACGA*GTACTGAGATCCCCT* (SEQ ID NO:21)
M. tb. Amplification Primer
(SEQ ID NO:19)

MULTIPLEX PRIMER SET 3 dnaJ Adapter Primer
GTACTGAGATCCCCT*GCCGGTGAACGA* (SEQ ID NO:22)
dnaJ Amplification Primer
(SEQ ID NO:17)
M. tb Adapter Primer
TCGGACAACACGTTG*AAGGCGTACTCGACC* (SEQ ID NO:23)
M. tb Amplification Primer
ACCGCATCGAATGCATGTCTCGGG*TGTACTGAGATCCCCT* (SEQ ID NO:24)

MULTIPLEX PRIMER SET 4 dnaJ Adapter Primer
GTACTGAGATCCCCT*TCGGACAACACGTTG* (SEQ ID NO:25)
dnaJ Amplification Primer
(SEQ ID NO:1)
M. tb Adapter Primer
GCCGGTGAACGA*AAGGCGTACTCGACC* (SEQ ID NO:26)
M. tb Amplification Primer
(SEQ ID NO:24)

Multiplex Primer Set 3 provided the best detection of the targets in both Mycobacterium tuberculosis and Mycobacterium avium. The primers of the invention may also be adapted for multiplex PCK as is known in the art, typically by conducting the PCR using the target binding sequences of a MAC-specific primer pair of the invention and a PCR primer pair having a different target specificity.

The MAC species from which the amplification products are generated may be identified or distinguished by hybridization to assay probes in the detection portion of the assay. For detection by hybridization, the detector probes are typically tagged with a detectable label. The detectable label is a moiety which can be detected either directly or indirectly as an indication of hybridization of the probe to the target nucleic acid. For direct detection of the label, probes may be tagged with a radioisotope and detected by autoradiography or tagged with a fluorescent moiety and detected by fluorescence as is known in the art. Alternatively, the probes may be indirectly detected by tagging with a label which requires additional reagents to render it detectable. Indirectly detectable labels include, for example, chemiluminescent agents, enzymes which produce visible reaction products and ligands (e.g., biotin, avidin, streptavidin, haptens, antibodies or antigens) which may be detected by binding to labeled specific binding partners (e.g., antibodies or antigens/haptens). Particularly useful labels include biotin (detectable by binding to labeled avidin or streptavidin) and enzymes such as horseradish peroxidase or alkaline phosphatase (detectable by addition of enzyme substrates to produce colored reaction products). Biotin and other ligands are also useful for tagging capture probes to allow immobilization of the capture probe and the complex to which it is hybridized on a solid phase by binding to the appropriate specific binding partner. Methods for adding such labels to, or including such labels in, oligonucleotides are well known in the art and any of these methods are suitable for use in the present invention.

One method for detecting amplification products employs polymerase extension of a primer specifically hybridized to the assay region. The primer is labeled as described above, e.g., with a radioisotope, so that the label is incorporated with the primer into an amplicon-specific extension product. Detection by primer extension is described by G. Walker, et al. (1992. *Nuc. Acids Res.* and *PNAS*, supra). SEQ ID NO:14 is particularly useful as a primer extension detector probe in conjunction with the amplification primers of the invention for detection of *M. avium*. SEQ ID NO:15 is particularly useful as a primer extension detector probe in conjunction with the amplification primers of the invention for detection of *M. intracellulare*. A second method for detecting amplification products is a chemiluminescent assay in which amplification products are detected using a biotinylated oligonucleotide capture probe and an enzyme-conjugated oligonucleotide detector probe as described by C. A. Spargo, et al. (1993. *Molec. Cell. Probes* 7, 395–404). After hybridization of these two probes to different sites in the assay region, the complex is captured on a streptavidin-coated microwell plate, and the chemiluminescent signal is developed and read in a luminometer. The chemiluminescent assay can be performed in less than two hours and is sensitive enough to detect as few as one pre-amplification target sequence. SEQ ID NO:14 and SEQ ID NO:15 are also useful as capture or detector probes in the assay.

In one embodiment of the invention, the capture and detector probes shown in Table 1 can be used to detect the presence of *M. avium* and/or *M. intracellulare* amplification products. Because the assay regions of the amplification products in *M. avium* and *M. intracellulare* differ from each other at several nucleotide positions, the species may be distinguished using only the capture and/or detector probes specific for the assay region of the desired target. These same assay probes also detect *M. paratuberculosis*. Alternatively, multiple species-specific assay probes may be combined in a single mixture for detecting the amplification products of all MAC species without distinguishing between them.

EXAMPLE 1

All pairwise combinations of upstream and downstream amplification primers shown in Table 1 were tested for amplification of the target ($10^6$ genomes) in *M. avium* by tSDA. The amplification reactions were carried out essentially as described in published European Patent Application No. 0 684 315. This resulted in a total of twelve amplification reactions in which each of the four upstream piers (SEQ ID NO:1–4) was paired with each of the three downstream primers (SEQ ID NO:5–7). Each primer pair produced a strong positive result in the assay, indicating amplification of the dnaJ target sequence.

EXAMPLE 2

The sensitivity of amplification and detection of *M. avium* and *M. intracellulare* dnaJ target sequences was determined using *M. avium* strain ATCC 25291 and *M. intracellulare* strain ATCC 13950. Mycobacterial genomic DNA was isolated and diluted in 50 ng of human placental DNA to final concentrations of $10^4$, $10^3$, $10^2$, 10 and 0 genomes in 50 µL tSDA reactions. The amplification primers were SEQ ID NO:1 and SEQ ID NO:6 and the bumper primers were SEQ ID NO:8 and SEQ ID NO:9. Thermophilic SDA was performed essentially as described in published European Patent Application No. 0 684 3 15 in a reaction mixture comprising 25 mM potassium phosphate pH 7.6, 100 µg/mL acetylated bovine serum albumin (BSA), 0.5 mM dUTP, 0.2 mM each dATP and dGTP, and 1.4 mM 2' deoxycytidine 5'-O-(1-thiotriphosphate) (α-thio dCTP), 12% glycerol, 6.5 mM magnesium acetate, 0.5 µM amplification primers, 0.05 µM bumper primers, 50 ng human placental DNA, 12.5 units Bst polymerase, 160 units BsoBI, 1 units uracil-N-glycosylase (UNG) and 2 units uracil-N-glycosylase inhibitor (Ugi).

Prior to addition of the enzymes and initiation of the amplification reaction, the samples were boiled for 2 min. The samples were then incubated at 41° C. for 2 min. and the UNG was added to degrade any contaminating amplicons. After a 30 min. incubation with UNG the samples were transferred to 52° C. for 5 min. The enzyme mix (Bst polymerase, BsoBI, Ugi and glycerol) was added and amplification was allowed to proceed for 30 min. at 52° C. The reaction was stopped by boiling for 5 min.

The amplification products were detected in a chemiluminescent assay essentially as described by Spargo, et al., supra. Alkaline phosphatase-labeled detector probes SEQ ID NO:12 and SEQ ID NO:13, biotinylated capture probes SEQ ID NO:10 and SEQ ID NO:11, and the samples were added to the well of a microtiter plate coated with streptavidin and incubated for 50 min. at 37° C. A low level of target amplification was expected in *M. hemophilum* in this system. However, the use of both capture probes in the detection portion of the assay resulted in both hybridizing to the assay region of *M. hemophilum*, thereby blocking access of the detector probe. The *M. hemophilum* target was therefore not detected. The capture probes may also be used individually with the corresponding detector probe for detecting individual species, particularly when detection of *M. hemophilum* targets is not a concern. The wells were then washed three times with stringency buffer. LUMIPHOS (Lumigen, Inc.) was added and the reaction was incubated for 30 min. at 37° C. Luminescence was detected in a luminometer and relative light units (RLUs) were recorded. An RLU reading of at least about 2–3 times background was considered positive. The results were as follows:

| SPECIES | INITIAL # OF GENOMES | RLUs |
| --- | --- | --- |
| *M. avium* | 10000 | 1008 |
|  | 1000 | 321 |
|  | 100 | 95 |
|  | 10 | 1 |
|  | 0 | 1 |
| *M. intracellulare* | 10000 | 365 |
|  | 1000 | 32 |
|  | 100 | 2 |
|  | 10 | 3 |
|  | 0 | 1 |

Assay sensitivity using this primer set was between 10 and 100 genomes for *M. avium* and between 100 and 1000 genomes for *M. intracellulare*. The amplification and detection sensitivity for the SEQ ID NO:2/SEQ ID NO:5 amplification primer pair was tested in a similar experiment, and resulted in a detection sensitivity of between 100 and 1000 initial genomes of *M. avium*.

EXAMPLE 3

Primer specificity was evaluated by amplifying the dnaJ target sequence in the twenty-eight MAC serovars (including strains of each serovar) described by Inderlied, et al., supra, using $10^5$ genomes per reaction. The *M. avium* strains tested were: *M. avium* type strain (ATCC 25291), 11907-300, B-92, 14141-1395 (ATCC 35716), 6195, Sparrow 185 (ATCC 25767), 34540-Wales, 14186-1424 (ATCC 35768), 13528-1079, 255546-759, SBJ#2, TMC 1461 (ATCC 1461), 1602-1965, 2993, 6194, 17548-286 (ATCC 1479 and W-552. The *M. intracellulare* strains tested were: ATCC 13950, 157 Manten, P-42 (ATCC 35762), 5509-Borstel (ATCC 25122), Edgar Boone (ATCC 35761), Dent (ATCC 35840), Yandle-Yandle, P-54 (ATCC 35763), P-40 (ATCC 35764), 72-808, 1244 Hillberry, 6845, 12645 and 23393. Two strains, the identities of which were unresolved according to molecular criteria and cultural properties by the International Working Group on Mycobacterial Taxonomy were also tested: Melnick (ATCC 35770) and 5154 O'Connor. P-49 (ATCC 35847) and Lane 3081 were also tested, but have since been identified by the International Working Group on Mycobacterial Taxonomy as *M. scrofulaceum*, which is not a member of the MAC. The tSDA and detection reactions were performed as in Example 2. By comparison to the RLU reading for the negative control (an amplification reaction containing only 50 ng of human placental DNA - RLU 0.93), one of the *M. scrofulaceum* strains and both unidentified strains were negative in the assay (RLU 2–6). The target was amplified and detected in all of the MAC species tested and produced a strongly positive signal (RLU 76-1874). The second *M. scrofulaceum* strain was weakly positive (RLU 27) but easily distinguished from the strong positive result of the MAC species. A similar specificity would be expected for the other amplification primer pairs, as the target binding sequences hybridize to the same region of the target as SEQ ID NO:1 and SEQ ID NO:6. The addition or deletion of 1–3 nucleotides at the 5' end of the target binding sequence should not change the specificity of the primer, but may alter assay sensitivity.

EXAMPLE 4

The primers of the invention were tested for species and genus cross-reactivity by amplifying $10^7$ genomes of each non-MAC species per reaction as in Example 2. *M. avium* (ATCC 25291) and *M. intracellulare* (ATCC 13950) (104 genomes per reaction) served as positive controls. The non-MAC species of mycobacteria tested were: *M. paratuberculosis* (Linda), *M. chelonae* (TMC1543), *M. fortuitum* (TMC 2808), *M. gastri* (LCDC 1301), *M. gordonae* (TMC 1318), *M. kansasii* (TMC 1201), *M. marinum* (LCDC 801), *M. microti* (LCDC 203), *M. scrofulaceum* (TMC 1302), *M. tuberculosis* (VA44), *M. xenopi* (LCDC 1901), *M. bovis* (CDC 52), *M. bovis-BCG* (CDC 4), *M. africanum* (ATCC 35711), *M. malmoense* (BDDIS 3472), *M. flavescens* (LCDC 2601), *M. terrae* (BDDIS 3010, *M. hemophilum* (ATCC 27548), *M. genevense* (PIR 21), *M. smegmatis* (TMC 1533), *M. szulgai* (TMC 1328), *M. szulgai* (VAH), *M. simiae* (BDDIS 2308), *M. simiae* (BDDIS 2300) and *M. simiae* (BDDIS 2301). By comparison to the negative control amplification reaction (50 ng of human placenta/DNA—RLU 0.9), all non-MAC species were negative (RLU 0.3–0.6) with the exception of a weak positive signal for the *M. malmoense* strain (RLU 4.6), a strong positive signal in one strain of *M. szulgai* (TMC 1328, RLU 2161), and a strong positive signal in one strain of *M. simiae* (BDDIS 2308, RLU 2404). The other strains of *M. szulgai* and *M. simiae* tested were clearly negative. *M. paratuberculosis*, a subspecies of *M. avium*, also gave a strong positive signal.

The non-mycobacteria species tested were: *Corynebacterium diphtheriae* (ATCC 11913), *Corynebacterium xerosis* (ATCC 373), *Corynebacterium pseudodiphtheriticum* (ATCC 10700), *Nocardia asteroides* (ATCC 3308), *Nocardia brasiliensis* (ATCC 19296), *Nocardia orientalis* (ATCC 19795), *Streptomyces somaliensis* (ATCC 13201), *Streptomyces griseus* (ATCC 10 137), *Streptomyces albus* (ATCC 3004), *Streptomyces gedanensis* (ATCC 4880), *Actinomyces israelii* (ATCC 10049), *Eubacterium lentum* (ATCC 43055), *Rhodococcus equi* (ATCC 6939), *Rhodococcus rhodochrous* (ATCC 13808), *Propionibacterium acnes* (ATCC 6919), *Actinoplanes auranticolor* (ATCC 15330), *Streptosporangium viridialbum* (ATCC 33328) and *Streptoverticillium alboverticillatum* (ATCC 29818). By comparison to the negative control, all of the non-mycobacteria genera tested were negative for amplification of the dnaJ target sequence (RLU 0.3–1.0). The results of these experiments demonstrate that the primers of the invention specifically amplify the target in species of the *M. avium* complex, without substantial amplification of the target sequence in either non-MAC species of mycobacteria or non-mycobacteria genera. A similar specificity would be expected for the other amplification primer pairs, as the target binding sequences hybridize to the same region of the target as SEQ ID NO:1 and SEQ ID NO:6. The addition or deletion of 1–3 nucleotides at the 5' end of the target binding sequence should not change the specificity of the primer, but may alter assay sensitivity.

---

What is claimed is:

1. An oligonucleotide consisting of a target binding sequence selected from the group consisting of the target binding sequences of SEQ ID NO:1, SEQ ID NO:2, SEQ ID NO:3, SEQ ID NO:4, SEQ ID NO:5, SEQ ID NO:6 and SEQ ID NO:7 and, optionally, a sequence required for an amplification reaction.

2. The oligonucleotide of claim 1 wherein the sequence required for the amplification reaction is a restriction endonuclease recognition site which is nicked by a restriction endonuclease during Strand Displacement Amplification.

3. The oligonucleotide of claim 2 selected from the group consisting of SEQ ID NO:1, SEQ ID NO:2, SEQ ID NO:3, SEQ ID NO:4, SEQ ID NO:5, SEQ ID NO:6 and SEQ ID NO:7.

4. An oligonucleotide consisting of SEQ ID NO:8 or SEQ ID NO:9.

5. A method for amplifying a target nucleic acid sequence of the *Mycobacterium avium* complex comprising:
   a) hybridizing to the target nucleic acid
      i) a first amplification primer consisting of a target binding sequence selected from the group consisting of the target binding sequences of SEQ ID NO:1, SEQ ID NO:2, SEQ ID NO:3, SEQ ID NO:4 and, optionally, a sequence required for an amplification reaction, and
      ii) a second amplification primer consisting of a target binding sequence selected from the group consisting of the target binding sequences of SEQ ID NO:5, SEQ ID NO:6 and SEQ ID NO:7 and, optionally, the sequence required for the amplification reaction, and;
   b) extending the hybridized first and second amplification primers on the target nucleic acid sequence whereby the target nucleic acid sequence is amplified.

6. The method of claim 5 further comprising detecting the amplified target nucleic acid by hybridization to a detector probe.

7. The method of claim 6 wherein the detector probe consists of SEQ ID NO:12, SEQ ID NO:13, SEQ ID NO:14 or SEQ ID NO:15 tagged with a detectable label.

8. The method of claim 6 wherein the amplified target nucleic acid sequence is captured for detection by hybridization to a capture probe.

9. The method of claim 8 wherein the capture probe consists of SEQ ID NO:10 or SEQ ID NO:11 tagged with a ligand.

10. The method of claim 5 wherein the sequence required for the amplification reaction is a recognition site for a restriction endonuclease which is nicked by the restriction endonuclease during Strand Displacement Amplification.

11. The method of claim 10 wherein the first amplification primer consists of SEQ ID NO:1, SEQ ID NO:2, SEQ ID NO:3 or SEQ ID NO:4 and the second amplification primer consists of SEQ ID NO:5, SEQ ID NO:6 or SEQ ID NO:7.

12. The method of claim 11 wherein the hybridized first and second amplification primers are displaced from the target nucleic acid by extension of a first bumper primer consisting of SEQ ID NO:8 and a second bumper primer consisting of SEQ ID NO:9.

13. The method of claim 5 wherein the target nucleic acid is amplified by the Polymerase Chain Reaction.

14. A method for amplifying a target nucleic acid sequence of the *Mycobacterium avium* complex comprising:
   a) hybridizing to the target nucleic acid
      i) a first amplification primer consisting of SEQ ID NO:1, SEQ ID NO:2, SEQ ID NO:3 or SEQ ID NO:4, and
      ii) a second amplification primer consisting of SEQ ID NO:5, SEQ ID NO:6 or SEQ ID NO:7, and;
   b) amplifying the target nucleic acid in a Strand Displacement Amplification reaction.

15. The method of claim 14 further comprising detecting the amplified target nucleic acid by hybridization to a detector probe.

16. The method of claim 15 wherein the detector probe consists of SEQ D NO:12, SEQ ID NO:13, SEQ ID NO:14 or SEQ ID NO:15 tagged with a detectable label.

17. The method of claim 15 wherein the amplified target nucleic acid is captured for detection by hybridization to a capture probe.

18. The method of claim 17 wherein the capture probe consists of SEQ ID NO:10 or SEQ ID NO:11 tagged with a ligand.

19. The method of claim 14 wherein the first amplification primer consists of SEQ ID NO:1 and the second amplification primer consists of SEQ ID NO:6.

20. The method of claim 19 wherein the hybridized first and second amplification primers are displaced from the target nucleic acid by extension of a first bumper primer consisting of SEQ ID NO:8 and a second bumper primer consisting of SEQ ID NO:9.

21. An oligonucleotide selected from the group consisting of SEQ ID NO:16, SEQ ID NO:17, SEQ ID NO:18, SEQ ID NO:20, SEQ ID NO:1, SEQ ID NO:21, SEQ ID NO:22, SEQ ID NO:23, SEQ ID NO:24, SEQ ID NO:25 and SEQ ID NO:26.

22. A method for simultaneously amplifying a first and a second target comprising:
   a) hybridizing a first amplification primer to the first target, the first amplification primer comprising the target binding sequence of SEQ ID NO:1 or SEQ ID NO:6 and a recognition site for a restriction endonuclease capable of nicking one strand of a double-stranded hemimodified recognition site for the restriction endonuclease, extending the first amplification primer to produce a first extension product and displacing the first extension product;
   b) hybridizing to the first extension product a first adapter primer consisting of the target binding sequence of SEQ ID NO:6 or the target binding sequence of SEQ ID NO:1 and a first adapter sequence substantially identical to a target binding sequence of a second amplification primer which hybridizes to the second target, the second amplification primer further comprising the recognition site for the restriction endonuclease, extending the first adapter primer to produce a second extension product and displacing the second extension product;

c) hybridizing the second amplification primer to the second target, extending the second amplification primer to produce a third extension product and displacing the third extension;

d) hybridizing to the third extension product a second adapter primer consisting of a target binding sequence which hybridizes to the third extension product and a second adapter sequence consisting of the target binding sequence of SEQ ID NO:1 or the target binding sequence of SEQ ID NO:6, extending the second adapter primer to produce a fourth extension product, displacing the fourth extension product and;

e) simultaneously amplifying the second and fourth extension products using the first and second amplification primers.

23. The method of claim 22 wherein a) the first adapter primer consists of SEQ D NO:16, the first amplification primer consists of SEQ ID NO:17, the second adapter primer consists of SEQ ID NO:18 and the second amplification primer consists of SEQ ID NO:19;

b) the first adapter primer consists of SEQ ID NO:20, the first amplification primer consists of SEQ ID NO:1, the second adapter primer consists of SEQ ID NO:21 and the second amplification primer consists of SEQ ID NO:19;

c) the first adapter primer consists of SEQ ID NO:22, the first amplification primer consists of SEQ ID NO:17, the second adapter primer consists of SEQ ID NO:23 and the second amplification primer consists of SEQ ID NO:24, or;

d) the first adapter primer consists of SEQ ID NO:25, the first amplification primer consists of SEQ ID NO:1, the second adapter primer consists of SEQ ID NO:26 and the second amplification primer consists of SEQ ID NO:24.

24. The method of claim 22 further comprising detecting the amplified first or second target.

25. The method of claim 22 wherein the first adapter primer consists of SEQ ID NO:22, the first amplification primer consists of SEQ ID NO:17, the second adapter primer consists of SEQ ID NO:23 and the second amplification primer consists of SEQ ID NO:24.

26. A method for simultaneously amplifying a first and a second target comprising:

a) hybridizing to the first target a first adapter primer consisting of the target binding sequence of SEQ ID NO:6 or the target binding sequence of SEQ ID NO:1 and a first adapter sequence substantially identical to a target binding sequence of a first amplification primer which hybridizes to the second target, the first amplification primer further comprising the recognition site for the restriction endonuclease, extending the first adapter primer to produce a first extension product and displacing the first extension product;

b) hybridizing a second amplification primer to the first extension product, the second amplification primer comprising the target binding sequence of SEQ ID NO:1 or SEQ ID NO:6 and a recognition site for a restriction endonuclease capable of nicking one strand of a double-stranded hemimodified recognition site for the restriction endonuclease, extending the first amplification primer to produce a second extension product and displacing the second extension product;

c) hybridizing to the second target a second adapter primer consisting of a target binding sequence which hybridizes to the second target and a second adapter sequence consisting of the target binding sequence of SEQ ID NO:1 or the target binding sequence of SEQ ID NO:6, extending the second adapter primer to produce a third extension product and displacing the third extension product;

d) hybridizing the first amplification primer to the third extension product, extending the first amplification primer to produce a fourth extension product, displacing the fourth extension product and;

e) simultaneously amplifying the second and fourth extension products using the first and second amplification primers.

* * * * *

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:

( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

CGATTCCGCT CCAGACTTCT CGGGGCCGGT GAACGA                                    36

( 2 ) INFORMATION FOR SEQ ID NO:2:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

CGATTCCGCT CCAGACTTCT CGGGCGCCGG TGAACGA                                   37

( 2 ) INFORMATION FOR SEQ ID NO:3:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

CGATTCCGCT CCAGACTTCT CGGGCCGCCG GTGAACGA                                  38

( 2 ) INFORMATION FOR SEQ ID NO:4:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

CGATTCCGCT CCAGACTTCT CGGGGCCGCC GGTGAACGA                                 39

( 2 ) INFORMATION FOR SEQ ID NO:5:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

ACCGCATCGA ATGCATGTCT CGGGCGGACA ACACGTTG                                  38

( 2 ) INFORMATION FOR SEQ ID NO:6:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

ACCGCATCGA ATGCATGTCT CGGGTCGGAC AACACGTTG                                 39

( 2 ) INFORMATION FOR SEQ ID NO:7:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

ACCGCATCGA ATGCATGTCT CGGGGTCGGA CAACACGTTG                                40

( 2 ) INFORMATION FOR SEQ ID NO:8:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

TTCCTTGCGC TTGG                            14

( 2 ) INFORMATION FOR SEQ ID NO:9:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

GCCAACCCGG ACAA                            14

( 2 ) INFORMATION FOR SEQ ID NO:10:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

GTGCGCCTCC GAC                              13

( 2 ) INFORMATION FOR SEQ ID NO:11:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

ACCGCCTTGA ATC                              13

( 2 ) INFORMATION FOR SEQ ID NO:12:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

ACGGCTTTGA ATC                              13

( 2 ) INFORMATION FOR SEQ ID NO:13:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

GTGCGCCTCG GAG                              13

( 2 ) INFORMATION FOR SEQ ID NO:14:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

TTCAAGGCGG TCTCC                                                15

( 2 ) INFORMATION FOR SEQ ID NO:15:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

TTCAAAGCCG TGTCG                                                15

( 2 ) INFORMATION FOR SEQ ID NO:16:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

AAGGCGTACT CGACCGCCGG TGAACGA                          27

( 2 ) INFORMATION FOR SEQ ID NO:17:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

CGATTCCGCT CCAGACTTCT CGGGTCGGAC AACACGTTG        39

( 2 ) INFORMATION FOR SEQ ID NO:18:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

TCGGACAACA CGTTGGTACT GAGATCCCCT                   30

( 2 ) INFORMATION FOR SEQ ID NO:19:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

ACCGCATCGA ATGCATGTCT CGGGTAAGGC GTACTCGACC       40

( 2 ) INFORMATION FOR SEQ ID NO:20:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:20:

AAGGCGTACT CGACCTCGGA CAACACGTTG     30

( 2 ) INFORMATION FOR SEQ ID NO:21:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:21:

GCCGGTGAAC GAGTACTGAG ATCCCCT     27

( 2 ) INFORMATION FOR SEQ ID NO:22:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:22:

GTACTGAGAT CCCCTGCCGG TGAACGA     27

( 2 ) INFORMATION FOR SEQ ID NO:23:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:23:

TCGGACAACA CGTTGAAGGC GTACTCGACC     30

( 2 ) INFORMATION FOR SEQ ID NO:24:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:24:

ACCGCATCGA ATGCATGTCT CGGGTGTACT GAGATCCCCT     40

( 2 ) INFORMATION FOR SEQ ID NO:25:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:25:

GTACTGAGAT CCCCTTCGGA CAACACGTTG     30

( 2 ) INFORMATION FOR SEQ ID NO:26:

( i ) SEQUENCE CHARACTERISTICS:
    ( A ) LENGTH: 27 base pairs

-continued ( B ) TYPE: nucleic acid
( C ) STRANDEDNESS: single
( D ) TOPOLOGY: linear ( x i ) SEQUENCE DESCRIPTION: SEQ ID NO:26:

GCCGGTGAAC GAAAGGCGTA CTCGACC                         2 7